(12) United States Patent
Huber

(10) Patent No.: US 6,489,486 B2
(45) Date of Patent: Dec. 3, 2002

(54) 2-HYDROXYPHENYL BENZOTRIAZOLES AS UV-A/B FILTERS

(75) Inventor: Ulrich Huber, Erlenbach (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/765,268

(22) Filed: Jan. 18, 2001

(65) Prior Publication Data

US 2001/0023293 A1 Sep. 20, 2001

(30) Foreign Application Priority Data

Feb. 21, 2000 (EP) .............................................. 00103592

(51) Int. Cl.$^7$ ........................................... C07D 249/18
(52) U.S. Cl. ...................................................... 548/259
(58) Field of Search ................................. 548/257, 259

(56) References Cited

U.S. PATENT DOCUMENTS

| | | | |
|---|---|---|---|
| 4,316,033 A | * 2/1982 | Ching et al. | 548/110 |
| 4,349,602 A | 9/1982 | Ching | 428/331 |
| 4,587,346 A | 5/1986 | Winter et al. | 548/260 |
| 4,812,575 A | 3/1989 | Vogl et al. | |
| 5,164,462 A | * 11/1992 | Yang et al. | 525/478 |
| 5,352,753 A | * 10/1994 | Yang et al. | 528/27 |

FOREIGN PATENT DOCUMENTS

GB    2 077 747 A    12/1981

OTHER PUBLICATIONS

Chemical Abstracts, CAS Registry No. 139079–27–9.
Chemical Abstracts, CAS Registry No. 207738–75–8.
Chemical Abstracts, CAS Registry Nos. 2170–39–0 and 2170–39–8.
Chemical Abstracts, CAS Registry No. 218900–69–7.
Chemical Abstracts, CAS Registry No. 102116–80–3.
Tiffany, "Partial para–Migration in the Allylic Rearrangement of o–Acetamidophenyl Allyl Ether and of o–Aminophenyl Allyl Ether," *Journal of the American Chemical Society*, vol. 70, pp. 592–594 (1948).

* cited by examiner

*Primary Examiner*—Joseph K. McKane
*Assistant Examiner*—Golam M. M. Shameem
(74) *Attorney, Agent, or Firm*—Bryan Cave LLP

(57) ABSTRACT

The present invention relates to a process for the manufacture of compounds of Formula (I):

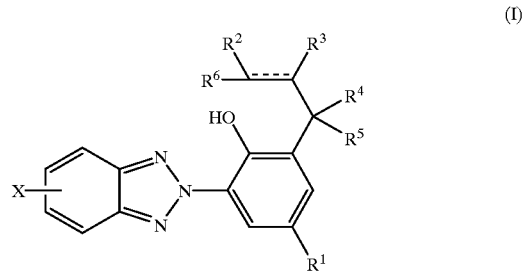

(I)

wherein $R^1$ is alkyl; $R^2$, $R^3$, $R^4$, $R^5$ and $R^6$ are, independently, hydrogen, alkyl or alkenyl; X is hydrogen, halogen, alkyl or alkoxy; and the dotted bond is an optional bond. The present invention also relates to novel light screening compositions containing certain of the compounds of Formula (I) and to certain novel compounds of Formula (I), as well as other novel 2-substituted phenyl-benzotriazole compounds.

14 Claims, No Drawings

2-HYDROXYPHENYL BENZOTRIAZOLES AS UV-A/B FILTERS

FIELD OF THE INVENTION

The present invention relates to a process for alkylating 2-hydroxyphenyl-benzotriazoles, which are effective in absorbing ultra violet radiation. In a further aspect, the present invention relates to novel alkylated 2-hydroxyphenyl-benzotriazoles, to novel cosmetic or dermatological sunscreen compositions containing alkylated 2-hydroxyphenyl-benzotriazoles, and to their use as UV screening agents.

BACKGROUND OF THE INVENTION

Winter et al., U.S. Pat. No. 4,587,346 discloses a process for alkylating 2-(2-hydroxy-5-methylphenyl)-2H-benzotriazoles by reaction with alkene compound ions in the presence of a catalyst. The process produces random mixtures of isomers.

UV screening compositions containing 2-hydroxyphenyl-benzotriazoles are described in European Patent Publications EP 0711778 A (Herve et al., U.S. Pat. No. 5,569,451), EP 0392883 A (Gerard et al., U.S. Pat. No. 5,089,250), Ching, U.S. Pat. Nos. 4,316,033 and 4,349,602, and International Patent Application WO 94/06404 (Hansenne et al., U.S. Pat. No. 5,089,250).

It has been found that alkylated 2-(2-hydroxy-5-methylphenyl)-2H-benzotriazoles can be obtained in substantially pure form. Further, it has been found that certain novel 2-hydroxyphenyl-benzotriazoles have improved solubility and extinction coefficients, and are more economical to prepare than those of the prior art quoted above.

SUMMARY OF THE INVENTION

The present invention is a process for the preparation of compounds of the formula:

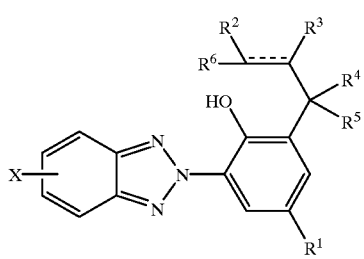

(I)

wherein $R^1$ is alkyl; $R^2$, $R^3$, $R^4$, $R^5$, and $R^6$ are, independently, hydrogen, alkyl or alkenyl; X is hydrogen, halogen, alkyl or alkoxy; and the dotted bond is an optional bond, which includes the steps of a) reacting a compound of the formula:

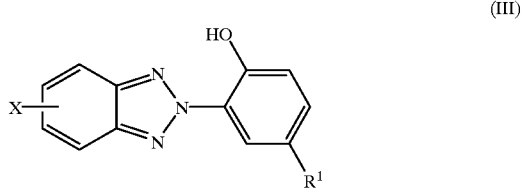

(III)

with a compound of the formula:

(IV)

to obtain a compound of the formula:

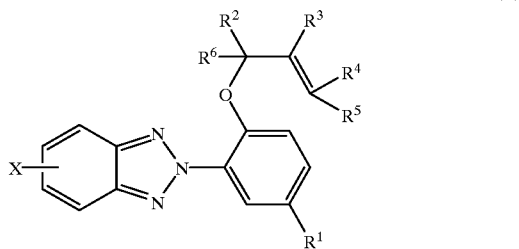

(II)

b) heating the compound of formula II obtained in step a) to yield a compound of the formula

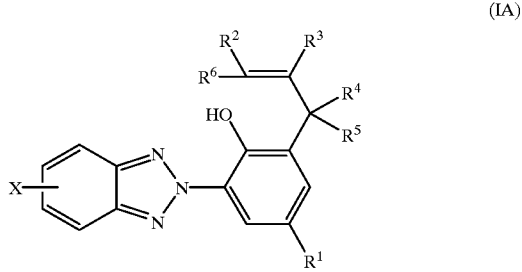

(IA)

and if desired, c) hydrogenating the double bond between $R^2$ and $R^3$ in the compound of formula I A to obtain a compound of formula I wherein the dotted bond is absent;

wherein in the above formulae IA, II, III and IV, $R^1$, $R^2$, $R^3$, $R^4$, $R^5$, $R^6$, X and the dotted line are as defined in formula I, and Y is a leaving group.

The following compounds are novel, and are also part of the present invention: compounds of formula I above, wherein X, $R^1$, $R^2$, $R^3$, $R^4$, $R^5$, $R^6$ and the dotted bond are as defined in claim 1, with the proviso that if the dotted bond is present, one of $R^2$, $R^4$, $R^5$, and $R^6$ is alkenyl, and if the dotted bond is absent, one of $R^2$ and $R^6$ is alkenyl or branched alkyl. In addition, the following compounds are also novel:

2-(Benzotriazole-2-yl)-4-methyl-6-(1-octen-3-yl)-phenol, 2-(Benzotriazole-2-yl)-4-methyl-6-(3-octen-2-yl)-phenol 2-(Benzotriazole-2-yl)-4-(1,1,3,3-tetramethylbutyl)-6-(1-hexen-3-yl)-phenol, 2-(Benzotriazole-2-yl)-4-methyl-6-(1-decen-3-yl)-phenol, 2-(Benzotriazole-2-yl)-4-methyl-6-(1-hexen-3-yl)-phenol, 2-(Benzotriazole-2-yl)-4-methyl-6-(1-dodecen-3-yl)-phenol, 2-(Benzotriazole-2-yl)-4-methyl-6- (1-hexadecen-3-yl)-phenol, 2-(Benzotriazole-2-yl)-4-methyl-6-(3-octyl)-phenol, 2-(Benzotriazole-2-yl)-4-(1,1,3,3-tetramethylbutyl)-6-(3-hexyl)-phenol, 2-(Benzotriazole-2-yl)-4-methyl-6-(3-hexyl)-phenol, 2-(Benzotriazole-2-yl)-4-methyl-6-(3-decyl)-phenol, 2-(Benzotriazole-2-yl)-4-methyl-6-(3-dodecyl)-phenol, 2-(Benzotriazole-2-yl)-4-methyl-6-(3-hexadecyl)-phenol, 2-(Benzotriazole-2-yl)-4-methyl-6-(3,7-dimethyl-2-octenyl)-phenol, 2-(Benzotriazole-2-yl)-4-methyl-6-(3,7-dimethyl-3-octyl)-phenol, 2-(Benzotriazole-2-yl)-4-methyl-6-(3,7-dimethyl-1-octen-3-yl)-phenol, 2-(Benzotriazole-2-yl)-4-methyl-6-(3,7-dimethyl-3-octyl)-phenol, 2-(Benzotriazole-2-yl)-4-methyl-6-(3,7-dimethyl-3-octen-2-yl)-phenol, and 2-(Benzotriazole-2-yl)-4-methyl-6-(3,7-dimethyl-2-octyl)-phenol.

Further examples of novel compounds of the present invention are:

2-(Benzotriazole-2-yl)-4-methyl-6-(3,7-dimethyl-2,6-octadienyl)-phenol, 2-(Benzotriazole-2-yl)-4-methyl-6-(3,7-dimethyl- 1,6-octadienyl)-phenol, and 2-(Benzotriazole-2-yl)-4-methyl-6-(3,7-dimethyl-3,6-octadienyl)-phenol.

Another aspect of the invention relates to novel cosmetic or dermatological UV light screening compositions containing a 2-hydroxyphenyl-benzotriazole of formula I above, wherein X, $R^1$, $R^2$, $R^3$, $R^4$, $R^5$, $R^6$, and the dotted bond are as defined in claim 1, with the proviso that either $R^4$ or $R^5$ is an alkyl having at least 2 carbon atoms, or is alkenyl. In yet another aspect, the invention relates to novel UV light screening compositions containing a 2-hydroxyphenyl-benzotriazole of formula I above, wherein X, $R^1$, $R^2$, $R^3$, $R^4$, $R^5$, $R^6$, and the dotted bond, are as defined in claim 1, with the proviso that either $R^4$ or $R^5$ is an alkyl having at least 2 carbon atoms or is an alkenyl; and at least one additional UV-A and/or UV-B screening agent. Finally, the present invention relates to a method for protecting hair or skin from damage caused by UV-radiation comprising administering to the hair or skin prior to exposure to a UV-radiation source a composition comprising an UV-radiation blocking amount of the novel 2-hydroxyphenyl-benzotriazoles as defined earlier, as UV light screening agents.

Especially preferred compounds of formula I for use as UV light screening agents are:

2-(Benzotriazole-2-yl)-4-methyl-6-(1-octen-3-yl)-phenol, 2-(Benzotriazole-2-yl)-4-(1,1,3,3-tetramethylbutyl)-6-(1-hexen-3-yl)-phenol, 2-(Benzotriazole-2-yl)-4-methyl-6-(3-octyl)-phenol, and 2-(Benzotriazole-2-yl)-4-(1,1,3,3-tetramethylbutyl)-6-(3-hexyl)-phenol.

The most preferred compound is 2-(Benzotriazole-2-yl)-4-methyl-6-(1-octen-3-yl)-phenol.

As used herein the term "alkyl" denotes saturated straight or branched chain hydrocarbon groups containing 1 to 21, preferably 1 to 8 carbon atoms, such as methyl, ethyl, propyl, isopropyl, butyl, sec. butyl, isobutyl, pentyl, neopentyl, hexyl, 2-ethyl-hexyl, and octyl. Similarly, the term "alkoxy" denotes saturated straight or branched chain hydrocarbon groups which are bound through an oxygen atom and which contain 1 to 21, preferably 1 to 8 carbon atoms, such as methoxy, ethoxy, propoxy, isopropoxy, butoxy, sec. butoxy, isobutoxy, pentyloxy, neopentyloxy, hexyloxy, 2-ethyl-hexyloxy and octyloxy. The term "alkenyl" denotes straight or branched chain hydrocarbon groups containing at least one double bond and 2 to 21, preferably 2 to 8, carbon atoms. Examples of such alkenyl groups are propen-2-yl, propen-3-yl, buten-3-yl, buten-4-yl, penten-4-yl, and penten-5-yl. The term "halogen" denotes fluoro, chloro, bromo and iodo.

A preferred group of compounds within formula I are those wherein the dotted bond is present. Also preferred are compounds of formula I wherein $R^5$ and $R^6$ are hydrogen. Further preferred are compounds wherein one of $R^2$, $R^3$, or $R^4$ is an alkyl having at least three carbon atoms, and the other two are hydrogen. The total number of carbon atoms in $R^2$ to $R^6$ is preferably 3 to 21, more particularly 3 to 9 carbon atoms, most preferably 3 to 5. Especially preferred are compounds of formula I wherein $R^2$ and $R^3$ are hydrogen and $R^4$ is an alkyl having 3 to 5 carbon atoms. $R^1$ is preferably methyl or 1,1,3,3-tetramethylbutyl. X is preferably hydrogen, methoxy or chloro, and most preferably hydrogen.

DETAILED DESCRIPTION OF THE INVENTION

In accordance with the novel process of this invention, the compounds of formula I are prepared as shown in Scheme 1 below:

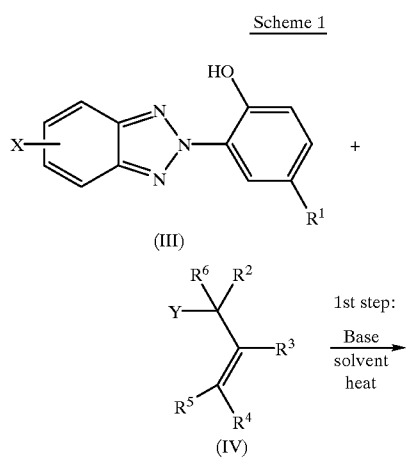

Scheme 1

-continued

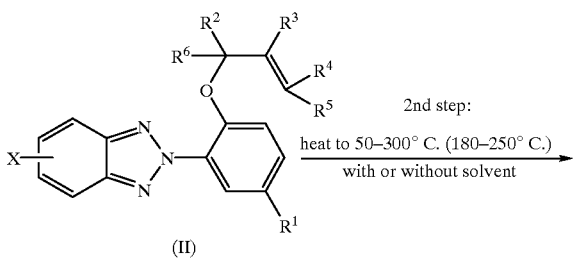

(II)

2nd step:
heat to 50–300° C. (180–250° C.)
with or without solvent

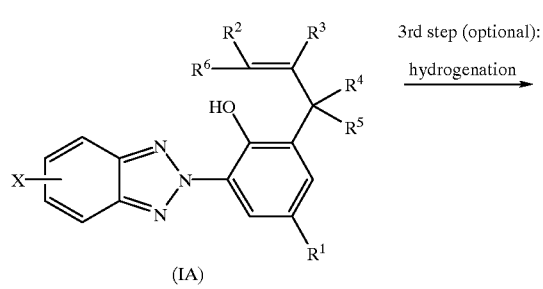

(IA)

3rd step (optional):
hydrogenation

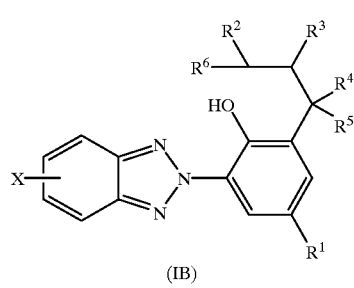

(IB)

In the first reaction step, the benzotriazolyl phenol is reacted with an alkene compound carrying a leaving group Y, such as halogen, e.g., chloro, bromo, or a sulfonyloxy group, e.g., tosyloxy or mesyloxy. The reaction can be carried out in a manner known per se for the alkenylation of phenolic hydroxy groups, i.e., in the presence of a base such as an alkali carbonate, e.g., sodium carbonate, an alkali hydroxide or alkali alcoholates, e.g., sodium methylate; an amine such as triethyl amine, N,N-dimethylamino pyridine or 1,4-diazabicyclo[2.2.2]octane (DABCO); in a polar solvent e.g., an alcohol such as n-butanol, an ether such as diethyleneglycol monomethyl ether, tetrahydrofuran or dioxan; or in dimethyl formamide, dimethyl sulfoxide, N,N-dimethyl propylene urea or 1-methyl pyrrolidone, or in a solvent which simultaneously may serve as a base, such as N,N-dimethylamino pyridine, at temperatures from room temperature up to the boiling point of the reaction mixture. If desired, the phenol ether obtained can be rearranged by heating, preferably to a temperature from 50 to 300° C. in a solvent, preferably a solvent that is conventionally used in Claisen rearrangements, e.g., diethyl aniline or trichloro benzene, to yield the corresponding compound of formula I wherein the dotted line (optional double bond) is present. The olefinic double bond can be hydrogenated in a manner known per se, e.g., with elemental hydrogen in the presence of a noble metal catalyst such as Pd, or with Rany-Ni, preferably with elemental hydrogen in the presence of an appropriate catalyst which does not attack the triazole ring, e.g., a partially inactivated noble metal catalyst such as a Lindlar catalyst.

The starting compounds of formulae III and IV are known or can be prepared by methods known per se or described hereinafter. For instance, compounds of formula III can be prepared by a reaction sequence that comprises converting an X-substituted o-nitro aniline to the corresponding diazonium salt by reaction with sodium nitrite, followed by a diazotation reaction with an $R^1$-substituted phenol to form the diazo compound, and reduction of the remaining nitro group with concomitant cyclisation to form the triazole ring. Compounds of formula IV can be prepared by following Scheme 2:

Scheme 2

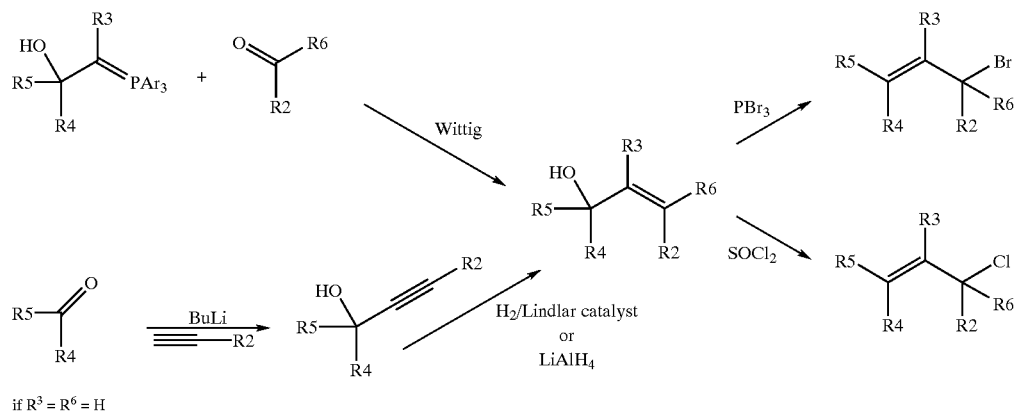

where $R^2$, $R^3$, $R^4$, $R^5$, and $R^6$ are defined as set forth above.

The phenol ether derivatives of formula II obtained in the first reaction step are novel compounds and as such, are also an object of the present invention.

The novel compounds of formula I have adsorption maxima in both the UV-A and the UV-B region. Furthermore, the compounds display good liposolubility and photostability.

For the preparation of light screening agents, especially preparations for dermatological or cosmetic use, such as skin protection and sunscreen formulations for everyday cosmetics, a compound of formula I can be incorporated into auxiliary agents, e.g., a cosmetic base, which are conventionally used for such formulations. Where convenient, other conventional UV-A and/or UV-B screening agents may also be added. The preparation of the light-screening agents is well known to the skilled artisan in this field. The amount of compounds of the general formula I and other known UV-filters is not critical. Suitable amounts are about 0.5 to about 12% (wt. %) of active ingredient, e.g., a compound of the general formula I and, if desired, any additional UV-A or UV-B screening agent.

Examples of UV B screening agents, i.e., substances having absorption maxima between about 290 and 320 nm, which come into consideration for combination with the compounds of the present invention are, for example, the following organic and inorganic compounds:

Acrylates, such as 2-ethylhexyl 2-cyano-3,3-diphenylacrylate (octocrylene, PARSOL® 340), ethyl 2-cyano-3,3-diphenylacrylate, and the like;

Camphor derivatives, such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid, and the like;

Cinnamate derivatives, such as octyl methoxycinnamate (PARSOL® MCX), ethoxyethyl methoxycinnamate, diethanolamine methoxycinnamate (PARSOL® Hydro), isoamyl methoxycinnamate, and the like, as well as cinnamic acid derivatives bonded to siloxanes;

Organosiloxane compounds containing benzalmalonate groups, as described in the European Patent Publications EP 0358584 B1 (Gerard et al., U.S. Pat. No. 5,053,290), EP 0538431 B1 (Frater et al., U.S. Pat. No. 5,403,944) and EP 0709080 A1, which are incorporated by reference as if recited herein in full;

Pigments, such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides, e.g., aluminum or zirconium oxides, or by organic coatings, e.g., polyols, methicone, aluminum stearate, or alkyl silane. Such coatings are well known in the art;

Imidazole derivatives, e.g., 2-phenyl benzimidazole sulfonic acid and its salts (PARSOL®HS). Salts of 2-phenyl benzimidazole sulfonic acid are, e.g. alkali salts such as sodium-or potassium salts, ammonium salts, morpholine salts, salts of primary, sec. and tert. amines like monoethanolamine salts, diethanolamine salts, and the like;

Salicylate derivatives, such as isopropylbenzyl salicylate, benzyl salicylate, butyl salicylate, octyl salicylate (NEO HELIOPAN OS), isooctyl salicylate or homomenthyl salicylate (homosalate, HELIOPAN), and the like;

Triazone derivatives, such as octyl triazone (UVINUL T-150), dioctyl butamido triazone (UVASORB HEB), and the like.

Examples of UV A screening agents, i.e., substances having absorption maxima between about 320 and 400 nm, which come into consideration for combination with the compounds of the present invention are, for example, the following organic and inorganic compounds:

Dibenzoylmethane derivatives, such as 4-tert. butyl-4'-methoxydibenzoyl-methane (PARSOL® 1789), dimethoxydibenzoylmethane, isopropyldibenzoylmethane, and the like;

Benzotriazole derivatives, such as 2,2'-methylene-bis-(6-(2H-benzotriazole-2-yl)-4-(1,1,3,3,-tetramethylbutyl)-phenol (TINOSORB M), and the like;

Pigments, such as microparticulated ZnO and the like. The term "microparticulated" refers to a particle size from about 5 nm to about 200 nm, particularly from about 15 nm to about 100 nm. The ZnO particles may also be coated by metal oxides, e.g., aluminum or zirconium oxides, or by organic coatings, e.g., polyols, methicone, aluminum stearate, or alkyl silane. Such coatings are well known in the art.

As dibenzoylmethane derivatives are photolabile, it may be desirable to photostabilize these UV-A screening agents. Thus, the term "conventional UV-A screening agent" also refers to dibenzoylmethane derivatives, e.g., PARSOL® 1789 stabilized by, e.g., 3,3-Diphenylacrylate derivatives, as described in the European Patent Publications EP 0 514 491 B1 and EP 0 780 119 A1;

Benzylidene camphor derivatives, as described in Deflandre et al., U.S. Pat. No. 5,605,680;

Organosiloxanes containing benzalmalonate groups, as described in the European Patent Publications EP 0358584 B1 (Gerard et al., U.S. Pat. No. 5,053,290), EP 0538431 B1 (Frater et al., U.S. Pat. No. 5,403,944) and EP 0709080 A1, which are incorporated by reference as if recited herein in full.

Any conventional preparation that corresponds to the necessary cosmetic requirements can be used as a cosmetic base within the scope of the present invention, such as creams, lotions, emulsions, salves, gels, solutions, sprays, sticks, and milks. For further examples of potential preparations, refer to *Development, Evaluation and Regulatory Aspects* (N. Y. Lowe, N. A. Shaath, Marcel Dekker, Inc. ed., New York and Basel, 1990). Due to their good lipophility, the compounds of formula I can be incorporated well into oil- and fat-containing cosmetic preparations.

The following Examples illustrate the invention in more detail, but do not limit the scope of the invention in any manner. In the Examples, "tlc." means thin layer chromatography.

EXAMPLES

Example 1 a) 8.5g (44.7 mmol) of 1-bromo-2-octene (prepared from 1-octene-3-ol by the method of L. Miginiac and B. Mauzé, Bull. Soc. Chim. France, 2544, 2547 (1968)) were slowly added to a mixture of 7g of 2-(benzotriazole-2-yl)-4-methyl-6-phenol (Tinuvin®P, CIBA SA.) in 35 ml of 1-methyl-pyrrolidone, 8.2 g of anhydrous sodium carbonate and 2 mg of potassium iodide under a nitrogen atmosphere. The reaction mixture was left to stir for two hours at room temperature, and then for 18 hours at 100° C. The reaction was traced by tlc. (hexane:ethylacetate=3:1). The reaction mixture was then cooled to 20° C., poured onto water and extracted (3x) with ethyl acetate. The combined organic phases were washed with water, 2N NaOH (2x), and brine, and then dried over sodium sulfate. After concentrating and drying in a high vacuum, 10.7 g of crude, liquid 2-(2-oct-2-enyloxy-5-methyl-phenyl)-2H-benzotriazole, as identified by NMR and MS, was obtained.

b) 4 g (11.9 mmol) of 2-(2-oct-2-enyloxy-5-methyl-phenyl)-2H-benzotriazole prepared as described above, in 5 ml of N,N-diethylaniline were heated to reflux (230° C.) under nitrogen atmosphere. The reaction was traced by tlc. (hexane:ethyl acetate=2:1). After 165 minutes, the reaction was complete, and a solution of 2N HCl was added to the cold reaction mixture, followed by extraction with ether (3x). The combined organic phases were washed with a 10% KOH solution, acidified to pH 3–4 with 5N HCl and extracted with ether. The combined ether phases were dried over sodium sulfate and concentrated to yield 3.75 g (94%) of a brown liquid. The brown liquid contained 8% of 2-(benzotriazole-2-yl)-4-methyl-6-(3-octen-2-yl)-phenol.

The 8% byproduct was analyzed by NMR (CDCl$_3$): 0.87 ppm (Tr/3Pr); 1.26–1.4 (M/7Pr); 2.05 (D x Tr/2Pr); 2.38 (S/3Pr); 4.03 (Q x D/1Pr); 5.57 (D x Tr/1Pr); 5.72 (D x D x Tr/1Pr); 7.05 (D/1Pr); 7.46 (M/2Pr); 7.90 (M/2Pr); 8.07 (D/1Pr) and 11.4 (S/1Pr), UV(CH$_2$Cl$_2$) 306 and 344 nm. After chromatography on silica gel (Merck) with hexane/diethyl ether, slightly yellow crystals of the main product were formed: m.p. 37–38° C.

UV(CH$_2$Cl$_2$) 306 nm (16'800) and 344 nm (16'555); MS: 335 (M$^+$), 264, 145 (100%), 117; NMR (CDCl$_3$): 0.87 ppm (Tr/3Pr); 1.26–1.4 (M/6Pr); 1.77 (D x Tr/2Pr); 2.38 (S/3Pr); 3.90 (D x Tr/1Pr); 5.05 (D/1Pr); 5.10 (D/1Pr); 6.04 (D x D x D/1Pr); 7.05 (D/1Pr); 7.46 (M/2Pr); 7.90 (M/2Pr); 8.07 (D/1Pr) and 11.4 (S/1Pr).

In a separate reaction, 1 g of the above starting material was heated without solvent in a Kugelrohr oven for 270 minutes at 220° C. 2-Benzotriazole-2-yl-4-methyl-6-(1-octen-3-yl)-phenol of ca. 95% purity was obtained in quantitative yield.

The product is easily mixable with cosmetic solvents, such as Cétiol LC (Cocoyl caprylate caprate). Irradiation at a high dilution (50 ppm) with a Heraeus 150 W Hg-lamp indicated the product was photostable.

Example 2 a) 5.8 g (35.7 mmol) of 1-bromo-2-hexene (prepared from 1-hexene-3-ol by the method of L. Miginiac and B. Mauzé, *Bull. Soc. Chim. France* 1968, 2544, 2547) were slowly added to 7.98 g (24.7 mmol) of 2-(benzotriazole-2-yl)-4-(1,1,3,3-tetramethyl-butyl)-6-phenol (Aldrich) in 40 ml of 1-methyl-pyrrolidone and 6.5 g of anhydrous sodium carbonate, under a nitrogen atmosphere. The reaction mixture was left to stir for two hours at room temperature and then for 18 hours at 80° C. The reaction was traced by tlc. (hexane:ether:CH$_2$Cl$_2$ =3:1:1). The reaction mixture was then cooled to 20° C. and distributed (3x) between water and ethyl acetate. The combined organic phases were washed with water, 2N NaOH (2x), and brine, and then dried over sodium sulfate. After concentration, a crude crystalline product was obtained, which was recrystallized from hexane to yield 6.17 g of 2-(2-hex-2-enyloxy-5-(1,1,3,3-tetramethylbutyl)-phenyl)-2H-benzotriazole, m.p. 80–81° C.

UV(CH$_2$Cl$_2$): 287 nm (16'305); MS: 405 (M$^+$), 323, 252 (100%).

b) 5.6 g (13.8 mmol) of 2-(2-hex-2-enyloxy-5-(1,1,3,3-tetramethylbutyl)-phenyl)-2H-benzotriazole, prepared as described above, in 100 ml of N,N-dimethylaniline were heated to reflux. The reaction was traced by tlc. (hexane:ethyl acetate=7:3). After 22 hours the reaction was complete. N,N-dimethylaniline was distilled off and the product freed from residual amine in a high vacuum to yield 4.7 g (84%) of 2-(benzotriazole-2-yl)-4-(1,1,3,3-tetramethylbutyl)-6-(1-hexen-3-yl)-phenol as an orange liquid.

UV(CH$_2$Cl$_2$): 305 nm (16'007) and 343 nm (14'359); MS: 405 (M$^+$), 334 (100%).

The product is easily mixable with cosmetic solvents, such as Cétiol LC (Cocoyl caprylate caprate). Irradiation at a high dilution (50 ppm) with a Heraeus 150w Hg-lamp indicated the product was photostable.

Example 3

0.5 g of 2-(benzotriazole-2-yl)-4-methyl-6-(1-octen-3-yl)-phenol and a trace of "Lindlar catalyst" (Fluka) in 20 ml of hexane was hydrogenated for 4 hours under normal hydrogen pressure. Then the reaction mixture was filtered and concentrated to yield (quantitatively) 2-(benzotriazole-2-yl)-4-methyl-6-(3-octyl)-phenol as a yellow liquid.

UV(CH$_2$Cl$_2$): 306 nm (14'602) and 346 nm (13'850); MS: 337 (M$^+$), 308, 266, 238 (100%).

The product is easily mixable with cosmetic solvents, such as Cétiol LC (Cocoyl caprylate caprate). Irradiation at a high dilution (50 ppm) with a Heraeus 150 W Hg-lamp indicated the product was photostable.

Example 4

2 g of 2-(benzotriazole-2-yl)-4-(1,1,3,3-tetramethylbutyl)-6-(1-hexen-3-yl)-phenol and a trace of "Lindlar catalyst" (Fluka) in 25 ml of hexane was hydrogenated for 5 hours under normal hydrogen pressure. Then the reaction mixture was filtered and concentrated to yield 2 g of 2-(benzotriazole-2-yl)-4-(1,1,3,3-tetramethylbutyl)-6-(3-hexyl)-phenol as an orange liquid.

UV(CH$_2$Cl$_2$): 306 nm (15'121) and 346 nm (13'120); MS: 407 (M$^+$), 336 (100%).

The product is easily mixable with cosmetic solvents, such as Cétiol LC (Cocoyl caprylate caprate). Irradiation at a high dilution (50 ppm) with a Heraeus 150 W Hg-lamp indicated the product was photostable.

Example 5

Preparation of an O/W anionic UV-B and UV-A sunscreen lotion:

A broad spectrum sunscreen lotion containing 4% of the compound of Example 4 was prepared as follows:

| wt. % | compound and supplier | chemical name |
|---|---|---|
| | | Part A |
| 3 | PARSOL ® MCX[1] | Octyl methoxycinnamate |
| 4 | product of Example 4 | |
| 3 | PARSOL ® 500[1] | 4-Methylbenzylidene camphor |
| 4 | PARSOL ® 1789[1] | 4-t-Butyl-4'-methoxy-dibenzoyl methane |
| 2 | Glyceryl monostearate | Glyceryl stearate |
| 2 | Cetyl alcohol extra | Cetyl alcohol |
| 2 | Ganex V-220[2] | PVP/Eicosene copolymer |

-continued

| wt. % | compound and supplier | chemical name |
|---|---|---|
| 4 | Ceraphyl 375[2)] | Isostearyl neopentanoate |
| 4 | Ceraphyl 847[2)] | Octyldodecyl stearoyl stearate |
| 2 | Amphisol K[1)] | Potassium cetylphosphate |
| 0.1 | Edeta BD | Disodium EDTA |
| 0.6 | Phenonip[3)] | Phenoxyethanol & Methyl-, Ethyl-, Propyl- & Butyl-paraben |
| | Part B | |
| 11.15 | deionized water | deionized water |
| 50 | Carbopol 934 1% solution[4)] | Carbomer |
| 5 | Propyleneglycol | 1,2-Propanediol |
| 0.15 | Nipagin M[3)] | Methylparaben |
| 3 | KOH (10%) | Potassium hydroxyde |
| q.s. | Perfume oil | Fragrance |

Part A is heated in a reactor to 85° C. When homogeneous, Part B is added to Part A, followed by the addition of preheated KOH (75° C.), and the cooling and degassing of the emulsion.

Example 6
Preparation of an O/W UV-B and UV-A sunscreen lotion:
A broad spectrum sunscreen lotion containing 2% of a compound of Example 3 was prepared as follows:

| wt. % | compound and supplier | chemical name |
|---|---|---|
| 2 | PARSOL ® MCX[1)] | Octyl methoxycinnamate |
| 2 | product of Example 3 | |
| 3 | PARSOL ® 1789[1)] | 4-t-Butyl-4'-methoxy-dibenzoyl-methane |
| 12 | Cétiol LC[6)] | Cocoyl-caprylate/caprate |
| 4 | Dermol 185[6)] | Isostearyl neopentanoate |
| 0.25 | Diethyleneglycol monostearate | PEG-2-stearate |
| 1 | Cetylalcohol | Cetylalcohol |
| 0.25 | MPOB/PPOB | Methyl-propylparabene |
| 0.1 | EDTA BD | EDTA-sodium salt |
| 1 | Amphisol DEA[1)] | Diethanolamine cetylphosphate |
| | Part B | |
| 20 | Permulene TR-1 (+%)[4)] | Acrylate C10–C30 Alkylacrylate |
| 48.6 | deionized water | deionized water |
| 5 | Propyleneglycol | 1,2-Propanediol |
| 0.8 | KOH (10%) | Potassium hydroxyde |

Part A is heated in a reactor to 85° C.
Part B is slowly added to Part A within 10 min., followed by the addition of KOH, and the cooling and degassing of the emulsion.

| Suppliers |
|---|
| 1) F. HOFFMANN - LA ROCHE LTD, CH-4070 Basel/Switzerland |
| 2) International Specialty Products ISP |
| 3) NIPA LABORATORIES LTD, Mid Glam. - CF38 2SN/England |
| 4) B.F. GOODRICH COMPANY, Brecksville - OH 44141/USA |
| 5) HENKEL K.G, Düsseldorf/Germany |
| 6) BERNEL Chemical Co. Inc. Englewood - NJ/USA |

The invention being thus described, it will be obvious that the same may be varied in many ways. Such variations are not to be regarded as a departure from the spirit and scope of the invention and all such modifications are intended to be included within the scope of the following claims.

We claim:

1. A compound of Formula (I):

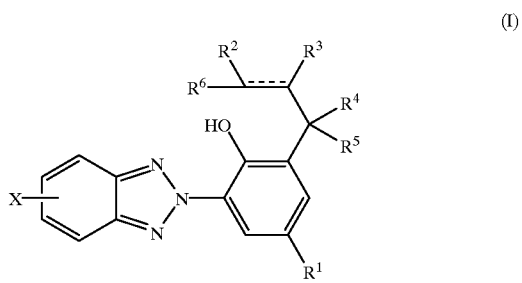

wherein $R^1$ is alkyl;

$R^2, R^3, R^4, R^5$, and $R^6$ are, independently, hydrogen, alkyl or alkenyl;

X is hydrogen, halogen, alkyl or alkoxy; and the dotted bond is an optional bond, with the proviso that if the dotted bond is present, one of $R^2, R^4, R^5$, and $R^6$ is alkenyl, and if the dotted bond is absent, one of $R^2$ and $R^6$ is alkenyl or branched alkyl.

2. A compound according to claim 1 wherein the dotted bond is present.

3. A compound according to claim 1 wherein the total number of carbon atoms in $R^2$ to $R^6$ is 3 to 5.

4. A compound according to claim 1 wherein one of $R^2$ to $R^4$ is an alkyl having at least three carbon atoms, and the other two of $R^2$ to $R^4$ are hydrogen.

5. A compound according to claim 1 wherein $R^2$ and $R^3$ are hydrogen.

6. A compound according to claim 1 wherein $R^4$ is an alkyl having 3 to 5 carbon atoms.

7. A compound according to claim 1 wherein $R^1$ is methyl or 1,1,3,3-tetramethylbutyl.

8. A compound according to claim 1 wherein X is hydrogen.

9. A compound according to claim 1 wherein the dotted bond is absent.

10. A compound according to claim 1 which is 2-(Benzotriazole-2-yl)-4-methyl-6-(1-octen-3-yl)-phenol.

11. A compound according to claim 1 which is 2-(Benzotriazole-2-yl)-4-methyl-6-(3-octen-2-yl)-phenol.

12. A compound according to claim 1 which is 2-(Benzotriazole-2-yl)-4-(1,1,3,3-tetramethylbutyl)-6-(1-hexen-3-yl)-phenol.

13. A compound according to claim 1 which is 2-(Benzotriazole-2-yl)-4-methyl-6-(3-octyl)-phenol.

14. A compound according to claim 1 which is 2-(Benzotriazole-2-yl)-4-( 1,1,3,3-tetramethylbutyl)-6-(3-hexyl)-phenol.

* * * * *